United States Patent [19]

Bauman

[11] 4,007,281
[45] Feb. 8, 1977

[54] PHARMACEUTICAL COMPOSITIONS CONTAINING QUATERNARY AMMONIUM COMPOUNDS

[75] Inventor: Robert Andrew Bauman, New Brunswick, N.J.

[73] Assignee: Colgate-Palmolive Company, New York, N.Y.

[22] Filed: Feb. 20, 1976

[21] Appl. No.: 659,618

Related U.S. Application Data

[60] Division of Ser. No. 134,827, April 16, 1971, which is a division of Ser. No. 712,968, March 14, 1968, Pat. No. 3,621,048, which is a continuation-in-part of Ser. No. 578,981, Sept. 13, 1966, abandoned.

[52] U.S. Cl. .............................. 424/300; 424/256; 424/322
[51] Int. Cl.$^2$ .......................................... A01N 9/20
[58] Field of Search ....... 260/455 A, 471 C, 482 C, 260/481 C, 470; 424/300

[56] References Cited

UNITED STATES PATENTS

| | | | |
|---|---|---|---|
| 2,642,450 | 6/1953 | Weijlard et al. | 260/455 A |
| 2,953,568 | 9/1960 | Werner | 260/455 A |
| 2,974,082 | 3/1961 | Collins | 260/455 A |
| 3,098,091 | 7/1963 | D'Amico | 424/300 |
| 3,100,223 | 8/1963 | Hopkins et al. | 424/300 |

*Primary Examiner*—Glennon H. Hollrah
*Attorney, Agent, or Firm*—Robert L. Stone; Murray M. Grill; Herbert S. Sylvester

[57] ABSTRACT

Quaternary ammonium carbamate, thiocarbamate, dithiocarbamate and carbamide compounds. Typical examples are

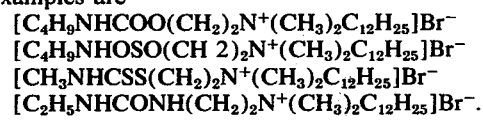

8 Claims, No Drawings

PHARMACEUTICAL COMPOSITIONS CONTAINING QUATERNARY AMMONIUM COMPOUNDS

This is a divisional of application Ser. No. 134,827 filed Apr. 16, 1971, which is a divisional of Ser. No. 712,968 filed Mar. 14, 1968 now U.S. Pat. No. 3,621,048 granted Nov. 16, 1971 which is a CIP of Ser. No. 578,981 filed Sept. 13, 1966, now abandoned.

The present invention relates to novel quaternary ammonium compounds and, more particularly, to quaternary ammonium compounds containing a carbamate, or a thiocarbamate, or a dithiocarbamate, or a carbamide group. The novel quaternary ammonium compounds of the present invention are useful in reducing caries, inhibiting acid formation in the oral cavity, in inhibiting formation of oral calculus, and/or as effective fungicides.

Novel compounds of the invention are superior to quaternary ammonium compounds, to carbamates and to thiocarbamates previously known to have some efficacy in in vitro anti-caries tests. They also reduce caries and inhibit formation in vivo in mammals.

It has been discovered that quaternary ammonium compounds having a carbamate, or a thiocarbamate, or a dithiocarbamate, or a carbamide group have greatest usefulness as bactericides against gram-positive organisms and as fungicides and as effective anti-caries and calculus inhibiting agents. The compounds of the present invention can be represented by the following formula:

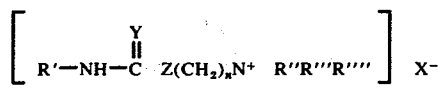

wherein
R' is selected from the group consisting of an alkyl group containing 1 to 22 carbon atoms, an aryl group, an aryl group substituted by halogen, i.e., Cl, Br, F, I, an aryl group substituted by alkyl containing 1 to 5 carbon atoms, and an aryl group substituted by alkoxy containing 1 to 5 carbon atoms;
R'' and R''' are each selected from the group consisting of acyclic aliphatic hydrocarbon radicals having 1 to 2 carbon atoms and hydrocarbon radicals that form a ring system including the $(CH_2)_nN$ group and R'' and R''';
R'''' is an alkyl group containing 1 to 22 carbon atoms, an aryl group substituted by halogen, i.e., Cl, Br, F, I; an aryl group substituted by alkyl containing 1 to 5 carbon atoms; an aryl group substituted by alkoxy group containing 1 to 5 carbon atoms, divalent aliphatic groups having up to 10 carbon atoms, divalent aryl groups, monovalent aryl group;
Y is selected from the group consisting of oxygen and sulfur;
Z is selected from the group consisting of oxygen, NH and sulfur;
X is a compatible anion such as $Cl^-$, $Br^-$, $I^-$, $SO_4Me^-$; and n is an integer 2 to 6.

When the $-(CH_2)_nNR''R'''-$ groups form a ring system, typically the ring system is quinuclidine

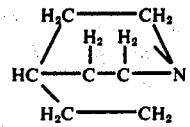

or piperidine,

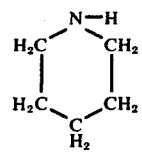

When the $-(CH_2)_nNR''R'''-$ groups do not form a ring system, R'' and R'''' may be the same or different; that is, both may be $CH_3$, or both may be $C_2H_5$ or one may be $CH_3$ and the other $C_2H_5$.

It is to be observed that the compounds generally described by the foregoing formula are effective against gram positive organisms such as Staph. aureus, Str. mitis S-3, Bacillus subtilis, Corynebacterium acnes, and against fungi, such as Candida albicans and Trichophyton mentagrophytes. Of the compounds represented by the general formula given hereinbefore, those compounds in which either R' or R'''' is a long chain alkyl group (10-16 carbon atoms) and the other of R' and R'''' is a short chain alkyl (1 to 4 carbon atoms) or aryl, or aralkyl group containing 1 to 5 carbon atoms in the alkyl moiety are particularly effective against gram-positive organisms. Of the compounds represented by the general formula provided hereinbefore, the compounds particularly effective against fungi are those in which R' is an aromatic group and particularly an aryl group or an aryl group substituted by halogen, and R'''' is a long chain alkyl group (10 to 18 carbon atoms).

The compounds of the invention which are most effective in reducing caries and inhibiting formation of oral calculus are those in which R'''' is a long alkyl chain having 10 to 16 carbon atoms. The compounds of the general formula given herein which are most effective in in vitro anti-caries are those in which one of R' or R'''' is a long alkyl chain of 10 to 14 carbon atoms and the other of R' or R'''' is an aryl group or a halogen-substituted aryl group or short alkyl chain of 1 to 4 carbon atoms and n is in the range of 2 to 6.

The thiocarbamate compounds can be prepared by converting the amino alcohol to the sodium salt thereof with metallic sodium in any suitable manner. An isothiocyanate is reacted with the aforesaid sodium salt. The reaction product is isolated in any suitable manner and quaternized with an alkylhalide or aralkyl halide.

The carbamate compounds can be prepared by reacting an isocyanate with the aminoalcohol, followed by quaternization with an alkyl or aralkyl halide.

The dithiocarbamate compounds can be prepared by reacting an isothiocyanate with the sodium salt of the aminoalkanethiol followed by quaternization with an alkyl or aralkyl halide.

The carbamide compounds can be prepared by reacting an isocyanate with the alkanediamine followed by quaternization with an alkyl or aralkyl halide.

The following examples illustrate the manner in which compounds of the invention are prepared.

EXAMPLE 1

2-hydroxyethyl dimethyldodecylammonium bromide, N-butylthiocarbamate is prepared in the following manner: Sodium (0.095 gr. atom) was powdered under 100 milliliters of xylene. 2-dimethylaminoethanol (0.095 mole) was added during 10 minutes and the mixture stirred until the sodium dissolved. Normal butyl isothiocyanate (0.10 mole) was added at room temperature (about 75° F.). After standing at ambient temperature (about 75° F.) for about 80 minutes the reaction mixture was poured into about 500 milliliters of water and the resultant slurry neutralized with 16 milliliters of concentrated hydrochloric acid. After removing the xylene, the aqueous layer was washed with diethyl ether and then made basic with sodium hydroxide. The oil is extracted with ether and recovered by evaporation or distillation of the ether. The residue, i.e., the product, O-(2-dimethylaminoethyl) N-butylthiocarbamate has a neutral equivalent of 205 (theory 204.3). A portion of the amine so obtained (0.01 mol) was mixed with 0.01 mol of 1-bromododecane and kept at ambient (room temperature —75° F.) for 2 weeks. The resultant crystalline mass was triturated with diethyl ether leaving 4.1 grams of product which was recrystallized from 30 milliliters of ethyl acetate, i.e., about seven times as much ethyl acetate as product by weight. The recovered crystals weighed 3.6 grams and had a melting point of 91° to 93° C.

| Analysis for $C_{21}H_{45}Br\ N_2OS$ Calculated | | Found |
|---|---|---|
| 55.61% | Carbon | 55.07% |
| 10.00% | Hydrogen | 10.01% |
| 6.18% | Nitrogen | 6.04% |

The infrared and nuclear magnetic resonance spectra agree with the following structural formula:

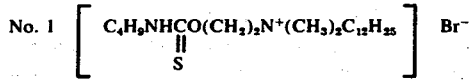

The thiocarbamate compounds for which structural formulas are given in the table below have been similarly prepared. All aromatic substitution is para. Thus,

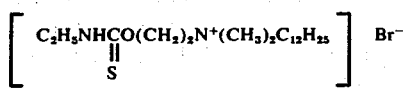

(compound 23 in the table below) is prepared using ethyl isothiocyanate in place of normal butyl isothiocyanate.

EXAMPLE 2

2-hydroxyethyldimethyldodecylammonium bromide, N-butylcarbamate is prepared in the following manner: A solution of 58 g. (0.65 mole) 2-dimethylaminoethanol in 150 ml. ether was treated over a period of 1.5 hours with 70 g. (0.71 mole) n-butyl isocyanate. After stirring another two hours the reaction mixture was stripped of ether and distilled in vacuum. The product, 2-dimethylaminoethyl N-butylcarbamate was collected at 106°/1.2 Torr. For quaternization 75 g. (0.40 mole) of the above prepared amine was combined with 105 g (0.42 mole) 1-bromododecane and allowed to stand stoppered for nine days. At this time the reaction mixture was a stiff gel with some crystalline portions. By solution in ethyl acetate (900 ml.) and chilling, 160 g. of product was obtained in crystalline form. After two more recrystallizations from ethyl acetate, the material melted at 64° C. to liquid crystals and to a liquid at 115° C.

Analysis for $C_{21}H_{15}BrN_2O_2$

| Analysis for $C_{21}H_{15}BrN_2O_2$ Calculated | | Found |
|---|---|---|
| 57.65 | Carbon | 57.87 |
| 10.37 | Hydrogen | 10.82 |

The infrared and nuclear magnetic resonance spectra agree with the following structural formula:

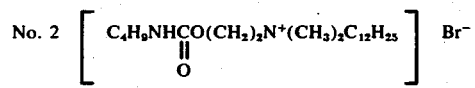

The carbamate compounds for which structural formulas are given in the table below have been similarly prepared. All aromatic substitution is para.

EXAMPLE 3

2-(Methyldithiocarbamyl) ethyldimethyldodecylammonium bromide was prepared as follows: A solution of 15.0 g. (0.105 mole) of 2-dimethylaminoethanethiol hydrochloride in 15 ml. of water was neutralized with 210 ml. of 1N sodium hydroxide solution and then treated immediately with 8.1 g. (0.11 mole) of methyl isothiocyanate dissolved in a few ml. of methanol. Following 30 minutes of stirring at room temperature, the reaction mixture was treated with 105 ml. of 1N hydrochloric acid. After 1 hour the precipitated solid was removed by filtration, dried, and recrystallized from benzene-Skellysolve B. The yield was 9.7 g. (54%), mp. 110°–112°.

A solution of 3.0 g. (0.017 mole) of the above-prepared 2-dimethylaminoethyl methyldithiocarbamate and 4.2 g. (0.017 mole) of 1-bromododecane in 25 ml. acetone was prepared and set aside for two weeks. The solid mass which had formed was recrystallized from anhydrous 3A alcohol, to recover 4.3 g. mp 174°–175°.

Analysis for $C_{18}H_{39}BrN_2S_2$

| Analysis for $C_{18}H_{39}BrN_2S_2$ Calculated | | Found |
|---|---|---|
| 50.56 | Carbon | 51.31 |
| 9.19 | Hydrogen | 9.30 |
| 6.55 | Nitrogen | 6.54 |

The infrared and nuclear magnetic resonance spectra agree with the following structural formula:

No. 3 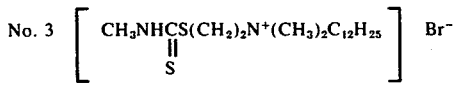

EXAMPLE 4

2-(Ethylureido)ethyldimethyldodecylammonium bromide was prepared as follows: Five grams (0.057 mole) of N,N-dimethylethylenediamine dissolved in 10 ml. of ether was treated dropwise with 4.3 g. (0.06 mole) of ethyl isocyanate dissolved in 10 ml. of ether. After 15 minutes the reaction mixture was diluted with more ether and saturated with hydrogen chloride gas. The precipitate was triturated with acetone and dried. In titrating with sodium chloride two end points were observed indicating it was the dihydrochloride of 1-ethyl-3-(2-dimethylaminoethyl)urea. By neutralization with sodium hydroxide, evaporation, extraction with ether, and evaporation 5.5 g. of free base was obtained.

1.6 g. (0.01 mole of the above prepared amine and 2.5 g. (0.01 mole) 1-bromododecane were dissolved in 25 ml. acetone and allowed to stand overnight. The mixture was then refluxed for 3½ hours. Evaporation of the solvent left a mixture of product and starting materials which was separated by ether extraction, the product being insoluble. The 1.6 g. material so obtained was recrystallized from ethyl acetate, m.p. 93.5°–95.3°.

Analysis for $C_{19}H_{42}BrN_3O$

| Analysis for $C_{19}H_{42}BrN_3O$ Calculated | | Found |
|---|---|---|
| 55.86 | Carbon | 55.78 |
| 10.37 | Hydrogen | 10.95 |
| 10.29 | Nitrogen | 10.20 |

The infrared and nuclear magnetic resonance spectra agree with the following structural formula:

No. 4 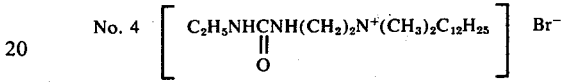

The following table lists additional compounds of the invention:

Table

| No. | Compound | Melting Point Degrees Centigrade |
|---|---|---|
| 5 | [$C_6H_5NHCOO(CH_2)_2N^+$ ($CH_3)_2CH_2C_6H_4Br$] $Br^-$ | 186–188 |
| 6 | [$C_6H_5NHCOO(CH_2)_2N^+$ ($CH_3)_2C_{12}H_{25}$] $Br^-$ | 144–145 |
| 7 | [$ClC_6H_4NHCOO(CH_2)_2N^+$ ($CH_3)_2CH_2C_6H_4Cl$] $Cl^-$ | 207–208 |
| 8 | [$ClC_6H_4NHCOO(CH_2)_2N^+$ ($CH_3)_2CH_2C_6H_4Br$] $Br^-$ | 199.5–201 |
| 9 | [$ClC_6H_4NHCOO(CH_2)_6N^+$ ($CH_3)_2CH_2C_6H_4Br$] $Br^-$ | 188.5–190 |
| 10 | [$ClC_6H_4NHCOO(CH_2)_6N^+$ ($CH_3)_2C_{12}H_{25}$] $Br^-$ | 104–105.3 |
| 11 | [$ClC_6H_4NHCOO(CH_2)_2N^+$ ($CH_3)_2$—$(CH_2)_5]_2$ $Br_2^-$ | 213–215 |
| 12 | [$ClC_6H_4NHCSO(CH_2)_2N^+$ ($CH_3)_2CH_2C_6H_4Cl$] $Cl^-$ | 162–163 |
| 13 | [$ClC_6H_4NHCSO(CH_2)_2N^+$ ($CH_3)_2CH_2C_6H_4Br$] $Br^-$ | 178.5–179.5 |
| 14 | [$ClC_6H_4NHCSO(CH_2)_3N^+$ ($CH_3)_2CH_2C_6H_4Br$] Br | 152–154 |
| 15 | [$ClC_6H_4NHCSO(CH_2)_6N^+$ ($CH_3)_2CH_2C_6H_4Br$] $Br^-$ | 167.5–168.5 |
| 16 | [$ClC_6H_4NHCSO(CH_2)_2N^+$ ($CH_3)_2C_{12}H_{25}$] $Br^-$ | 140.5–142.5 |
| 17 | [$ClC_6H_4NHCSO(CH_2)_3N^+$ ($CH_3)_2C_{12}H_{25}$] $Br^-$ | 150–151 |
| 18 | [$ClC_6H_4NHCSO(CH_2)_6N^+$ ($CH_3)_2C_{12}H_{25}$] $Br^-$ | 106–108.5 |
| 19 | [$ClC_6H_4NHCSO(CH_2)_2N^+$ ($CH_3)_2C_{18}H_{37}$] $Br^-$ | 146–150 |
| 20 | [$C_{12}H_{25}NHCSO(CH_2)_2N^+$ ($CH_3)_2CH_2C_6H_4Br$] $Br^-$ | 118.5–120.5 |
| 21 | [$C_{12}H_{25}NHCSO(CH_2)_2N^+$ ($CH_3)_3$] $I^-$ | 170–172 |
| 22 | [$CH_3NHCSO(CH_2)_2N^+$ ($CH_3)_2C_{12}H_{25}$] $Br^-$ | 73.0–75.5 |
| 23 | [$C_2H_5NHCSO(CH_2)_2N^+$($CH_3)_2C_{12}H_{25}$] $Br^-$ | 94.5–97.0 |
| 24 | [$C_4H_9NHCSO(CH_2)_2N^+$($CH_3)_2C_{10}H_{21}$] $Br^-$ | 93–96 |
| 25 | [$C_4H_9NHCSO(CH_2)_2N^+$($CH_3)_2C_{14}H_{29}$] $Br^-$ | 94–96 |
| 26 | [$CH_3NHCSO(CH_2)_6N^+$($CH_3)_3$] $I^-$ | 115.5–117 |
| 27 | [$CH_3NHCSO(CH_2)_6N^+$($CH_3)_2C_{12}H_{25}$] $Br^-$ | 81.5– |
| 28 | [$C_2H_5NHCSO(CH_2)_2N^+$($CH_3)_2CH_2C_6H_4Br$] $Br^-$ | 141–142.5 |
| 29 | [$C_2H_5NHCSO(CH_2)_2N^+$($CH_3)_2(CH_2$-$)_5]$ $_2$ $Br_2^-$ | 186.5–187 |
| 30 | [$C_2H_5NHCOO(CH_2)_2N^+$($CH_3)_2C_{12}H_{25}$] $Br^-$ | 67–69 |
| 31 | [$C_2H_5NHCOO(CH_2)_6N^+$($CH_3)_2C_{12}H_{25}$] $Br^-$ | oil |
| 32 | 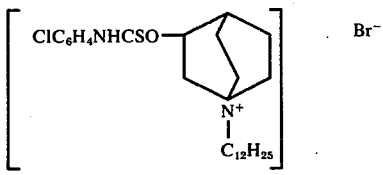 | 62–64 |
| 33 | 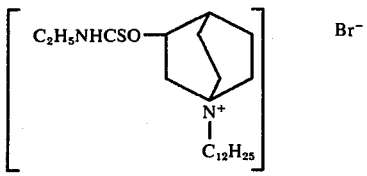 | oil |
| 34 | 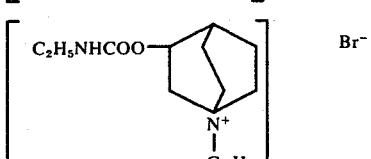 | oil |
| 35 | [$CH_3NHCSO(CH_2)_2$ $N^+(CH_3)_2C_{14}H_{29}$] $Br^-$ | 73.5–77 |

Table-continued

| No. | Compound | Melting Point Degrees Centigrade |
|---|---|---|
| 36 | $[CH_3NHCSO(CH_2)_2N^+(CH_3)_2C_{10}H_{21}]\ Br^-$ | 72–75 |
| 37 | $[ClC_6H_4NHCOO(CH_2)_2N^+(CH_3)_2C_{12}H_{25}]\ Br^-$ | 177–179 |
| 38 | $[CH_3NHCOO(CH_2)_2N^+(CH_3)_2C_{12}H_{25}]\ Br^-$ | 85.5–88 |
| 39 | $[CH_3NHCOO(CH_2)_2N^+(CH_3)_2C_{14}H_{29}]\ Br^-$ | 107–108 |
| 40 | $[CH_3NHCOO(CH_2)_3N^+(CH_3)_2C_{12}H_{25}]\ Br^-$ | 72.5–77 |
| 41 | $[CH_3NHCOO(CH_2)_3N^+(CH_3)_2C_{14}H_{29}]\ Br^-$ | 75–77 |
| 42 | $[C_2H_5NHCOO(CH_2)_2N^+(CH_3)_2C_{14}H_{29}]\ Br^-$ | 98–98.5 |
| 43 | $[C_6H_{11}NHCOO(CH_2)_2N^+(CH_3)_2C_{12}H_{25}]\ Br^-$ | 128.5–131 |
| 44 | $[C_6H_{11}NHCOO(CH_2)_2N^+(CH_3)_2C_{14}H_{29}]\ Br^-$ | 123–128 |

When submitted to a series of tests to determine their ability to prevent acid formation in incubated saliva both as is and/or as adsorbed upon protein and/or their ability to prevent growth of Streptococcus sp. HS-6 in a halo test, the compounds which are highly effective are numbers 1–4, 6, 16, 21–24, 27, 30, 31, and 33–44 of the above list of compounds of the general formula.

The tests set forth in Examples 5 and 6 below evidence the effectiveness of the compounds of the invention in reducing caries and inhibiting formation of calculus.

EXAMPLE 5

The following test was conducted with compounds 2, 23, 30, and 40 of the above list of compounds to determine their ability to reduce caries in animals. Caries-susceptible hamsters bred either from the Keyes strain or the NIDR (National Institute for Dental Research) strain in groups of 15 males and 15 females per control group and per each test group were fed ad lib a Mitchell cariogenic diet and received constant deionized water. Each day each hamster's teeth were swabbed 30 seconds by cotton tipped swabs, the control group with water and each test group with its test solution. After 6 weeks of swabbing the animals were sacrificed, and the defleshed heads were scored by a modified version of the Keyes scoring method. Mean averages and percentage changes from the control were determined and tested statistically to determine the significance.

| Compound | Concentration Test Solution | Caries Reduction % | |
|---|---|---|---|
| | | Males | Females |
| 23 | 1% | −55.4 | −62.2 |
| | 1% | −54.7 | −33.9 |
| | 0.5% | −44.2 | −69.2 |
| | 0.25% | −30.5 | −57.8 |
| 30 | 1% | −71.4 | −46.3 |
| 40 | 1% | −62.2 | −58.6 |
| 2 | 0.5% | −23.2 | −40.0 |

The results set forth above indicated the significant effectiveness of the quaternary compounds of the invention in reducing caries formation.

EXAMPLE 6

To show the effectiveness of compounds 2 and 23 in inhibiting the development of dental calculus, littermated Sprague-Dawley rats, 60 days old, in groups of 15 males and 15 females were fed a Zipkin-McClure calculus diet. For 2 to 3 weeks the teeth of each animal were swabbed for thirty seconds each day with a test solution or water for the control group. The animals were then sacrificed, defleshed and scored by Baer's method for calculus. The results were analyzed by Student's $t$ test and in the results quoted were 99% significant.

| Compound | Concentration Test Solution | Caries Reduction % | |
|---|---|---|---|
| | | Males | Females |
| 2 | 0.5% | −71 | −58 |
| 23 | 0.5% | −66 | −40 |

The results set forth above indicated the significant effectiveness of the quaternary compounds of the invention in inhibiting formation of oral calculus.

When compounds of the instant invention are intended for use in compositions which reduce formation of caries and inhibit formation of oral calculus, they are typically incorporated in oral preparations in effective amounts up to about 5% by weight, preferably 0.1–1% and most preferably 0.25–0.5% by weight of the oral preparation. Typically, the oral preparation is a dentifrice, such as a dental cream, tablet or powder, containing as a vehicle about 20–95% by weight of a water-insoluble polishing material, preferably including water-insoluble phosphate such as dicalcium phosphate, tricalcium phosphate, trimagnesium phosphate. The dentifrice may also include water; binders such as glycerine, sorbitol, propylene glycol, and polyethylene glycol 400; detergents; gelling agents such as Irish moss and sodium carboxymethyl cellulose; additional antibacterial agents; coloring or whitening agents; preservatives; silicones; chlorophyll compounds; additional ammoniated materials; flavoring or sweetening materials; and compounds which provide fluorine-containing ion such as sodium fluoride, stannous fluoride and sodium monofluorophosphate.

The oral preparation may also be a liquid such as mouth rinse which typically contains 20–99% by weight of an aqueous alcohol vehicle, the alcohol being a cosmetically acceptable and nontoxic alcohol such as ethanol or isopropyl alcohol and being present in amount of about 5–30% by weight of the oral preparation.

Such oral preparations are typically applied by brushing the teeth or rinsing the oral cavity for 30–90 seconds at least once daily. Typical oral preparations of the invention which can be applied in this manner are set forth below.

Example 7

| Dental Cream | % |
|---|---|
| Compound 23 | 0.50 |
| Nonionic detergent (Millox 120) | 2.00 |
| Glycerine | 22.00 |
| Sodium pyrophosphate | 0.25 |
| Carboxymethyl cellulose | 0.85 |
| Sodium saccharin | 0.20 |
| Sodium benzoate | 0.50 |
| Calcium carbonate (precipitated) | 5.00 |

Example 7-continued

| Dental Cream | % |
|---|---|
| Dicalcium phosphate dihydrate | 46.75 |
| Flavor | 0.80 |
| Water | 21.15 |

Example 8

| Mouth Wash | % |
|---|---|
| Compound 23 | 0.25 |
| Nonionic detergent (Pluronic F-68) | 1.00 |
| Ethyl alcohol (containing flavor) | 15.00 |
| Glycerine | 10.00 |
| Saccharin | 0.02 |
| Water | 73.73 |

The antimicrobial effectiveness of the compounds of the invention was evidenced in the tests set forth in Examples 9 and 10, below.

EXAMPLE 9

To illustrate the antibacterial character of compounds of the instant invention the following halo test was performed. The cariogenic strain of streptococcus (HS6) obtained from NIDR was grown in fluid thioglycollate medium at 37° C. for 24 hours. A 2% inoculum was added to fluid thioglycollate agar at 45° C. After thorough mixing it was dispersed in 20 ml. aliquots into sterile petri dishes. A ¼-inch diameter sterile paper disc was saturated with a solution of the test compound and placed in firm contact with this agar. Then 20 ml. of uninoculated fluid thioglycollate agar was poured into the petri dishes to reduce the oxygen tension. The dishes were incubated for 24 hours at 37° C. The results which are averages of duplicate determinations are reported as mm. of inhibition of bacterial growth around the disc.

| | Halo Test Results | | |
|---|---|---|---|
| Compound | Halo, mm. | Compound | Halo, mm. |
| 1 | 20 | 23 | 35 |
| 3 | 28 | 24 | 34 |
| 4 | 29 | 27 | 27 |
| 6 | 21 | 29 | 27 |
| 7 | 26 | 30 | 36 |
| 8 | 36 | 31 | 34 |
| 9 | 27 | 33 | 28 |
| 11 | 28 | 34 | 30 |
| 12 | 36 | 36 | 33 |
| 13 | 31 | 38 | 31 |
| 14 | 51 | 39 | 27 |
| 15 | 26 | 40 | 27 |
| 22 | 43 | 41 | 25 |

These halo tests evidenced anti-gram positive bacterial effectiveness of compounds of the invention.

EXAMPLE 10

The anti-microbial nature of the compounds was shown by a standard test tube serial dilution test in which an appropriate number of test tubes of broth containing decreasing concentrations of the test agent was inoculated with the test organism. After a suitable period of incubation the tubes were examined for the presence or absence of growth. The activity of the test agent was the lowest concentration which inhibited the growth of the organism and is expressed as the minimal inhibitory concentration (M.I.C.) in μg/ml.

| | Results (M.I.C.) | | | | | |
|---|---|---|---|---|---|---|
| Compound | S. aureus | S. mitis (S-3) | B. subtilis | C. acnes | C. albicans | T. mentogrophytes |
| 1 | 1.56 | 1.56 | 0.2 | 1.56 | 6.25 | 125 |
| 6 | 0.39 | 3.12 | 0.39 | 0.78 | 6.25 | 3.12 |
| 16 | 0.39 | 0.39 | 0.39 | 0.78 | 1.56 | 0.98 |
| 17 | <0.05 | 0.78 | <0.05 | 1.56 | 3.12 | 3.12 |
| 18 | 0.39 | <0.2 | 0.78 | 0.39 | 3.12 | 31.2 |
| 21 | 1.56 | 3.12 | 0.78 | 0.78 | 12.5 | 7.8 |
| 23 | 1.56 | 3.12 | 0.78 | 1.56 | 12.5 | 15.6 |
| 25 | <0.05 | 0.78 | 0.2 | 1.56 | 0.78 | 1.56 |
| 27 | 0.78 | 3.12 | 0.2 | 1.56 | 12.5 | 6.25 |
| 32 | <0.05 | 0.2 | 0.1 | 1.56 | 3.12 | 6.25 |
| 35 | 0.78 | 0.78 | 0.39 | 1.56 | 3.12 | 7.8 |
| 44 | 0.78 | 1.56 | 3.12 | 3.12 | 3.12 | 7.8 |

These dilution tests evidence the effectiveness of compounds of the invention against gram-positive bacteria and fungi.

When used against bacteria or fungi, compounds of the instant invention may be applied directly to the surface to be protected or may be dissolved in a pharmaceutical carrier. Typically, an effective amount, e.g. 0.1 to about 10% by weight of the compound, is included in an inert carrier and a dispersing or surface active agent. Alternatively, an effective amount, e.g. 0.1 to about 10% by weight, may be incorporated into a solid carrier which may be inert, such as talc, clay, diatomaceous earth, flour, etc.

Although this invention has been described with reference to specific examples, it will be apparent to one skilled in the art that various modifications may be made thereto which fall within its scope.

I claim:

1. A pharmaceutical composition comprising an effective amount of a chemical compound effective against gram positive microorganisms represented by the formula

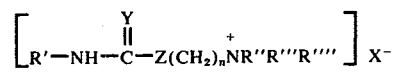

where
R' is selected from the group consisting of an alkyl group containing 1 to 22 carbon atoms, a phenyl group, a phenyl group substituted by an alkyl group containing 1 to 5 carbon atoms and a phenyl group substituted by an alkoxy group containing 1 to 5 carbon atoms and a phenyl group substituted by halogen; selected from the group consisting of chlorine and bromine R" and R''' are each selected from the group consisting of an alkyl group containing 1 to 2 carbon atoms;

R"" is selected from the group consisting of an alkyl group containing 10 to 22 carbon atoms, a phenyl group substituted by halogen selected from the group consisting of chlorine and bromine, a phenyl group substituted by an alkyl group containing 1 to 5 carbon atoms, a phenyl group substituted by an alkoxy group containing 1 to 5 carbon atoms, a divalent phenyl group and a monovalent phenyl group;

Y is selected from the group consisting of oxygen and sulfur;

Z is selected from the group consisting of oxygen and sulfur, at least one of Y and Z being sulfur;

$n$ is an integer 2 to 6; and

X is a compatible anion selected from the group consisting of chloride, bromide, iodide and methosulfate; said compound being admixed with a pharmaceutically acceptable carrier.

2. The pharmaceutical composition as claimed in claim 1 wherein R"" as an alkyl group selected from the group consisting of $C_{10}H_{21}$, $C_{12}H_{25}$ and $C_{14}H_{29}$ and R' is selected from the group consisting of $CH_3$, $C_2H_5$, $C_4H_9$, $C_6H_5$ and $ClC_6H_4$.

3. The pharmaceutical composition as claimed in claim 1 wherein R"" is selected from the group consisting of $C_{12}H_{25}$ and $C_{18}H_{37}$ and R' is selected from the group consisting of $C_6H_5$ and $ClC_6H_4$.

4. The pharmaceutical composition as claimed in claim 1 wherein Y is sulfur and Z is oxygen.

5. The pharmaceutical composition as claimed in claim 1 where said compound is represented by the formula:

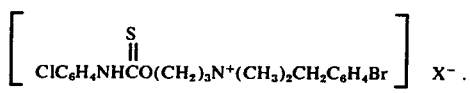

6. The pharmaceutical composition as claimed in claim 1 wherein said compound is represented by the formula:

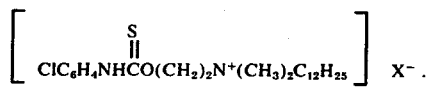

7. The pharmaceutical composition as claimed in claim 1 wherein said compound is represented by the formula:

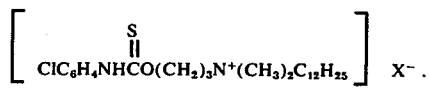

8. The pharmaceutical composition as claimed in claim 1 wherein said compound is represented by the formula:

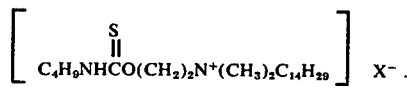

* * * * *